United States Patent
Hommes et al.

(10) Patent No.: US 10,240,142 B2
(45) Date of Patent: Mar. 26, 2019

(54) METHOD OF PRODUCING NANOBIOCATALYSTS

(71) Applicant: INOFEA GMBH, Basel (CH)

(72) Inventors: Gregor Hommes, Weil am Rhein (DE); Philippe Corvini, Leymen (FR); Alessandro Cumbo, Basel (CH); Patrick Shahgaldian, Saint Louis (FR); Yves Dudal, Hégenheim (FR)

(73) Assignee: INOFEA AG, Basel (CH)

( * ) Notice: Subject to any disclaimer, the term of this patent is extended or adjusted under 35 U.S.C. 154(b) by 516 days.

(21) Appl. No.: 14/764,008

(22) PCT Filed: Jan. 29, 2014

(86) PCT No.: PCT/EP2014/051739
§ 371 (c)(1),
(2) Date: Jul. 28, 2015

(87) PCT Pub. No.: WO2014/118247
PCT Pub. Date: Aug. 7, 2014

(65) Prior Publication Data
US 2015/0361416 A1    Dec. 17, 2015

(30) Foreign Application Priority Data
Jan. 30, 2013 (EP) .................................... 13153276

(51) Int. Cl.
*C12N 11/14* (2006.01)
*B82Y 5/00* (2011.01)
*C12N 9/02* (2006.01)

(52) U.S. Cl.
CPC .............. *C12N 11/14* (2013.01); *B82Y 5/00* (2013.01); *C12N 9/0061* (2013.01); *C12Y 110/03002* (2013.01)

(58) Field of Classification Search
None
See application file for complete search history.

(56) References Cited

FOREIGN PATENT DOCUMENTS

| CN | 101294157 | 10/2008 |
|---|---|---|
| WO | WO 2004/081208 A1 | 9/2004 |

OTHER PUBLICATIONS

Ping He, et al., "The on-line synthesis of enzyme functionalized silica nanoparticles in a microfluidic reactor using polyethylenimine polymer and R5 peptide", Nanotechnology, IOP, Bristol, GB, vol. 19, No. 31, Jun. 24, 2008, p. 315603.

Gregor Hommes, et al., "Production of a robust nanobiocatalyst for municipal wastewater treatment", Bioresource Technology, vol. 115, Nov. 8, 2011, pp. 8-15.

Galliker, P., et al., "Laccase-modified silica nanoparticles efficiently catalyze the transformation of phenolic compounds", Journal of Colloid and Interface Science, Academic Press, New York, NY, US, vol. 349, No. 1, May 16, 2010, pp. 98-105.

Salis, A., et al., "Laccase from Pleurotus sajor-caju on functionalised SBA-15 mesoporous silica: Immobilisation and use for the oxidation of phenolic compounds", Journal of Molecular Catalysis. B, Enzymatic, Elsevier, Amsterdam, NL, vol. 58, No. 1-4, Dec. 27, 2008, pp. 175-180.

Fernando Bautista L., et al., "Immobilization strategies for laccase from Trametes versicolor on mesostructured silica materials and the application to the degradation of naphthalene", Bioresource Technology, Elsevier BV, GB, vol. 101, No. 22, Nov. 1, 2010, pp. 8541-8548.

Rekuc A, et al., "Very stable silica-gel-bound laccase biocatalysts for the selective oxidation in continuous systems", Bioresource Technology, Elsevier BV, GB, vol. 101, No. 7, Apr. 1, 2010, pp. 2076-2083.

Cabana H, et al., "Immobilization of laccase from the white rot fungus *Coriolopsis polyzona* and use of the immobilized biocatalyst for the continuous elimination of endocrine disrupting chemicals", Bioresource Technology, Elsevier BV, GB, vol. 100, No. 14, Mar. 28, 2009, pp. 3447-3458.

Crestini C, et al., "Oxidative functionalisation of lignin by layer-by-layer immobilised laccases and laccase microcapsules", Applied Catalysis A: General, Elsevier Science, Amsterdam, NL, vol. 372, No. 2, Oct. 29, 2009, pp. 115-123.

*Primary Examiner* — Robert J Yamasaki
(74) *Attorney, Agent, or Firm* — Hoffmann & Baron, LLP

(57) ABSTRACT

A method of producing nanobiocatalysts includes: suspending a support material in a liquid medium; functionalizing a surface of the support material by mixing the suspended support material with a functionalizer for a first predefined time at a first predefined temperature, wherein a first broth results; applying a protein directly in the first broth after the first predefined time; mixing the protein with the first broth and incubating the protein for a second predefined time at a second predefined temperature, wherein a second broth results; immobilizing the incubated protein onto the functionalized surface of the support material, wherein a third broth results; filtering the third broth; and gathering a retentate of the filtering. By directly processing the first and second broths allows for providing a continuous process and production of the nanobiocatalysts, which can be optimized regarding time, water, chemical and energy consumption. Also, problems related to thixotrophy can be minimized.

26 Claims, 1 Drawing Sheet

METHOD OF PRODUCING NANOBIOCATALYSTS

CROSS-REFERENCE TO RELATED APPLICATIONS

This application is the U.S. National Phase of International Patent Application No. PCT/EP2014/051739, filed on 29 Jan. 2014, which claims benefit of European Patent Application No. 13153276.4, filed on 30 Jan. 2013, the contents of which are incorporated herein by reference in their entirety.

TECHNICAL FIELD

The present invention relates to the production of biocatalysts of nanometer scale. Such nanobiocatalysts can be used in a broad variety of applications in different technical fields.

BACKGROUND ART

In recent years the use of biocatalysts of nanometer scale, so called nanobiocatalysts has attracted increasing interest for various purposes in various fields of application.

For example, for the treatment of municipal or other wastewater it has been shown that removing pollutants such as pesticides, industrial surfactants, pharmaceuticals and hormonally active compounds collectively being referred to as emerging organic contaminants (EOGs) from the water by using nanobiocatalysts can be particularly efficient (see, e.g., [1]). In particular, suitable nanobiocatalysts can comprise a support material on which an enzyme is bound wherein the enzyme is catalyzing a transformation process in which EOCs are removed, reduced or made ineffective.

For the industrial use of nanobiocatalysts for various purposes comparably large amounts of suitable nanobiocatalysts have to be available. Thereby, the costs involved for producing nanobiocatalysts is a major issue in order that they are applied in the respective industrial processes. For example, [1] describes methods for producing a nanobiocatalyst at a comparably low enzyme and chemical consumption which consumption can be one major cost driver. Particularly, the described methods focus on efficiently immobilizing the enzyme on the support material. However, for large scale or multi-kilo scale production of nanobiocatalysts these methods still are not economically and ecologically satisfying particularly regarding their efficiency. Also, in these methods often problems regarding thixotrophy caused by the characteristics of the product can arise, particularly when being scaled up, such that comparably elaborate workarounds have to implemented, if possible at all.

Therefore, there is a need for a method allowing the production of nanobiocatalysts at comparably large scales and particularly at multi-kilo scales.

SUMMARY

According to the invention this need is settled by a method as it is defined by the features of independent claim 1. Preferred embodiments are subject of the dependent claims.

In particular, the gist of the invention is the following: A method of producing nanobiocatalysts comprises the following steps: suspending a support material in a liquid medium; functionalizing a surface of the support material by mixing the suspended support material with a functionalizer for a first predefined time at a first predefined temperature wherein a first broth results; applying a protein directly in the first broth after the first predefined time; mixing the protein with the first broth and incubating the protein for a second predefined time at a second predefined temperature wherein a second broth results; immobilizing the incubated protein onto the functionalized surface of the support material wherein a third broth results; filtering the third broth; and gathering a retentate of the filtering.

By directly processing the first and second broths the method according to the invention allows for providing a continuous process and production of the nanobiocatalysts. Thereby, the production can be optimized regarding time, water, chemical and energy consumption. Also, the method according to the invention allows for a nanobiocatalysts production in which problems related to thixotrophy can be minimized. These effects can drastically increase the efficiency of the process thereby making production of nanobiocatalysts at a comparably high rate possible. Furthermore, the method according to the invention also allows for saving resources such that efficiency can also be increased in this regard.

In the method according to the invention the support material preferably is suspended in water as liquid medium. The term "water" in this context can relate to any type of water such as distilled water, pure water, deionized water, salted water and the like. In particular, water can be regular tab water. By using water as liquid medium which is possible in the method according to the invention, the process can be performed in a cost effective, ecological and efficient manner.

Preferably, the support material comprises fumed silica nanoparticles. Fumed silica nanoparticles can be available as bulk material and can provide beneficial criteria of an immobilization support material, i.e. high surface area, porosity, chemical resistance, purity, non-hazardous. In particular, such nanoparticles made of a biocompatible porous inorganic material allow for leaving the protein efficiently accessible. Fumed silica nanoparticles can particularly be beneficial due to their comparably large specific surface area, negligible swelling, comparably high stability, comparably low toxicity and comparably low price.

Preferably, the mixture of the suspended support material and the functionalizer comprises about $$1 \frac{g}{L}$$

to about $$100 \frac{g}{L}$$

fumed silica nanoparticles, preferably about $$40 \frac{g}{L}$$

to about $$55 \frac{g}{L}$$

fumed silica nanoparticles and particularly about $$50 \frac{g}{L}$$

fumed silica nanoparticles. The term "about" used herein in connection with an attribute or a value particularly also defines exactly the attribute or exactly the value, respectively. Furthermore, in the context of a given numerate value or range this term refers to a value or range that is, e.g., within 20%, within 10%, within 5%, or within 2% of the given value or range. Such concentrations of the suspended support material allow for efficiently performing the method according to the invention and to prevent severe problems due to thixotrophy effects even when using fumed silica nanoparticle as support material.

Preferably, the functionalizer is an organosilane or an aminosilane or particularly 3-Aminopropyltriethoxysilane (APTES). Further, the mixture of the suspended support material and the functionalizer preferably comprises about 0.001 mM to about 1 mM functionalizer particularly about 0.18 mM to about 0.27 mM functionalizer. Also, the first predefined time preferably is in a range of about 1 minute to about 24 hours, preferably in a range of about 10 hours to about 15 hours and particularly is about 12 hours, wherein the first predefined temperature preferably is within a biologically compatible range, preferably in a range of about 4° C. to about 105° C., more preferably in a range of about 18° C. to about 25° C. and particularly in a range of about 20° C. to about 21° C. Still further, pH preferably is adjusted to a predefined pH value when the suspended support material is mixed with the functionalizer for the first predefined time at the first predefined temperature, wherein the predefined pH value preferably is within a biologically compatible range, preferably in a range of about 3 to about 9, more preferably in a range of about 7 to about 8 and particularly about 7.5. Thereby, pH preferably is adjusted by applying a pH active compound and particularly a saturated citric acid solution which allows for easy ecological adjustment of the pH.

Using a functionalizer, preferably such a functionalizer, preferably in such a concentration, preferably during such a time range, preferably at such a temperature and preferably at such a pH, allows for efficiently functionalizing the surface of the support material and thereby increasing incubation and immobilization of the protein on the surface of the support material in a following step. Thereby, each single one of these preferred aspects of the functionalization can increase overall efficiency at comparably low resource consumption of the functionalization wherein combinations thereof and in particular a combination of all these preferred aspect can be particular beneficial.

For example, in order to create anchor points for the subsequent cross linking of enzyme and support material, silanization can be applied to cover the surface of the fumed silica through self-assembly. The surfaces of fumed silica can be silanized because they contain hydroxyl groups which attack and displace the alkoxy groups on the silane thus forming a covalent —Si—O—Si— bond. By using APTES it can be possible to coat the fumed silica efficiently.

Preferably, the protein is an enzyme and more preferably laccase. The use of the enzyme in the method according to the invention allows for producing nanobioparticles and in particular nanobiocatalysts which can be used in various applications. In particular, the use of laccase allows for efficiently producing nanobiocatalysts suitable for treating wastewater, e.g. by reducing its emerging organic contaminants (EOGs).

The mixture of the first broth and the protein preferably comprises about 0.01 mg to about 1 mg total protein per functionalized fumed silica nanoparticle and particularly about 0.15 mg total protein per functionalized fumed silica nanoparticle. Further, the second predefined time is in a range of about 1 minute to about 24 hours, preferably in a range of about 1 hour to about 3 hours and particularly is about 2 hours. Still further, the second predefined temperature is within a biologically compatible range, preferably in a range of about 3° C. to about 7° C. and particularly about 5° C.

Preferably applying such a concentration, preferably during such a time range and preferably in such a temperature range allows for efficiently incubating the protein on the surface of the support material and thereby increasing immobilization of the protein on the surface of the support material in a following step. Thereby, each single one of these preferred aspects of the incubation can increase overall efficiency of the incubation wherein combinations thereof and in particular a combination of all these preferred aspect can be particular beneficial. Like this an efficient, resource saving production of respective nanobiocatalysts is possible.

Preferably, the incubated enzyme is immobilized onto the functionalized surface of the support material by applying an immobilizer to the second broth and mixing the immobilizer and the second broth for a third predefined time at a third predefined temperature resulting in the third broth. The immobilizer preferably is a bifunctional crosslinker, particularly glutaraldehyde. Thereby, from about 0.001 mol to about 1 mol and particularly about 0.053 mol crosslinker preferably is applied per liter of the second broth. Further, the third predefined time preferably is in a range of about 20 hours to about 30 hours and particularly is about 24 hours. Still further, the third predefined temperature is within a biologically compatible range, preferably in a range of about 18° C. to about 25° C. and particularly in a range of about 20° C. to about 21° C.

Preferably applying such an immobilizer, preferably in such a concentration, preferably during such a time range and preferably in such a temperature range allows for efficiently immobilizing the protein on the surface of the support material and thereby increasing immobilization of the protein on the surface of the support material. Thereby, each single one of these preferred aspects of the immobilization can increase overall efficiency of the incubation wherein combinations thereof and in particular a combination of all these preferred aspect can be particular beneficial. Like this, an efficient, resource saving production of respective nanobiocatalysts is possible.

In a preferred embodiment of the method according to the invention, the third broth is continuously filtered. Continuously, filtering the third broth allows for continuously providing the whole process such that an efficient production of biocatalysts is possible. Thereby, filtering of the third broth preferably is performed by using a single shaft disk filtration unit, wherein the single shaft disk filtration unit preferably comprises plural rotatable ceramic filter discs. Such a single shaft disk filtration unit allows for an efficient filtering of the third broth in a continuous process. Thereby, the single shaft disk filtration unit preferably comprises a pressure air system arranged to remove retentate from the filter discs. Such a pressure air system can be a suitable means for conveniently and completely removing the retentate such that the produced nanobiocatalysts can efficiently be gathered.

A filtrate or permeate of the filtering of the third broth preferably is disposed. Since the product of the process, i.e. the nanobiocatalysts are contained in the retentate, the filtrate or permeate can be disposed which allows for reusing the process devices for further processing.

In a preferred embodiment, functionalizing of the surface of the support material, mixing the enzyme with the first broth and incubating the enzyme as well as immobilizing incubated enzyme onto the functionalized surface of the support material is performed in a synthesis container which is equipped with a stirrer. Such a process conduct allows for a particular cost effective, efficient application of the method according to the invention. Thereby, the single shaft disk filtration unit preferably is connected to the synthesis container by a broth tube and by a retentate tube, wherein during filtering of the third broth the retentate is delivered from the single shaft disk filtration unit to the synthesis container via the retentate tube and the third broth is delivered from the synthesis tube to the single shaft disk filtration unit via the broth tube.

In certain embodiments the method described above as well as all aspects described in this context can also be used for producing other biomolecules than biocatalysts.

These and other aspects of the invention will be apparent from and elucidated with reference to the embodiment(s) described hereinafter.

BRIEF DESCRIPTION OF THE DRAWINGS

The method according to the invention is described in more detail hereinbelow by way of examples and with reference to the attached drawings, in which.

DETAILED DESCRIPTION/EXAMPLES

Figure 1:
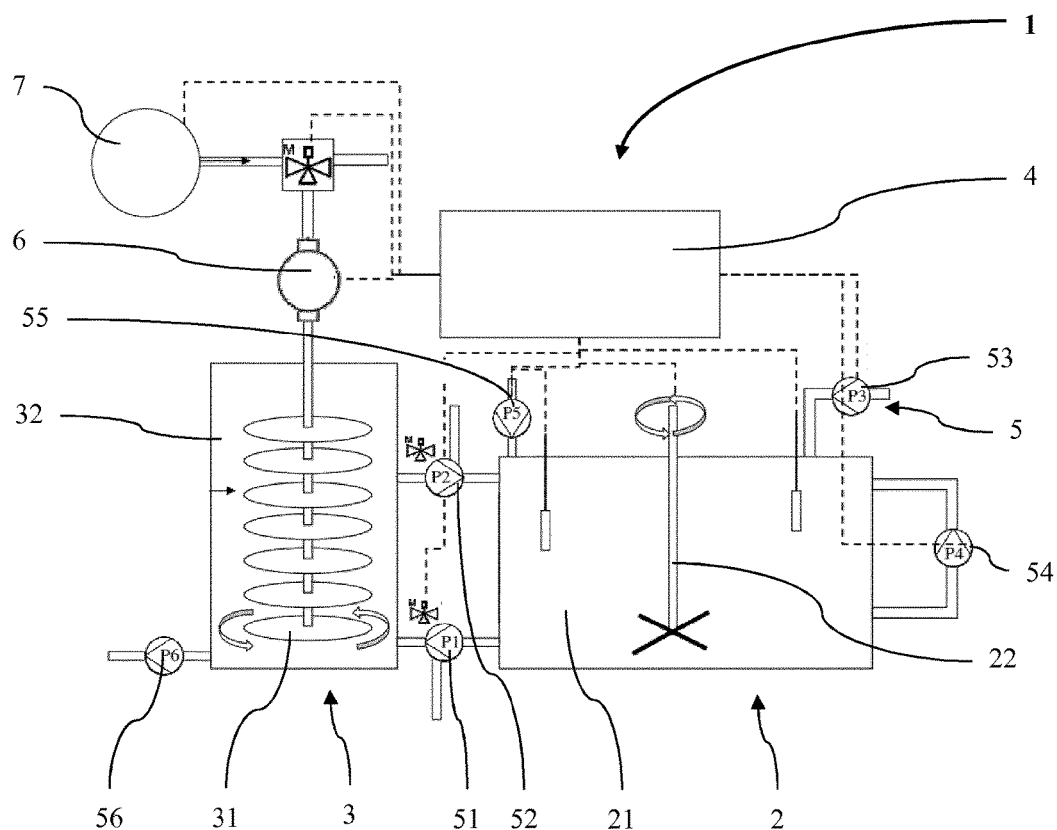
FIG. 1 shows a schematic view of an apparatus for producing nanobiocatalysts with an embodiment of the method according to the invention.

FIG. 1 shows an embodiment of an apparatus 1 for performing an embodiment of the method according to the invention in order to produce nanobiocatalysts. The apparatus 1 comprises a synthesis unit 2 being connected via two transfer pipes to a filtration unit 3 wherein one of the transfer pipes is arranged to provide media from the synthesis unit 2 to the filtration unit 3 and the other one of the transfer pipes is arranged to provide media in the opposite direction. The synthesis unit 2 has a synthesis vessel 21 provided with a stirrer 22. The filtration unit 3 has a filtration vessel 32 provided with a plurality of rotatable filtration discs 31 arranged along a longitudinal axis. The filtration discs 31 are connected with an air compartment 7 via a motor 6.

The apparatus 1 is equipped with a plurality of pumps 5, wherein a first pump 51 and a second pump 52 are arranged to provide media between the synthesis unit 2 and the filtration unit 3 via the transfer pipes and to provide a retentate or an effluent, respectively, out of the apparatus 1. A third pump 53 is arranged for providing tab water into the synthesis vessel 21 via a water pipe and a fourth pump 54 for circulation media inside the synthesis vessel 21 via a circulation pipe. A fifth pump 55 is arranged for providing a citric acid solution into the synthesis vessel 21 and sixth pump 56 for providing product out of the filtration vessel 32.

The first pump 51, the second pump 52 and the sixth pump 56 together form a first pressure system for adjusting the pressure conditions in the filtration unit 3. Similarly, the first pump 51, the second pump 52, the third pump 53, the fourth pump 54 and the fifth pump 55 together form a second pressure system for adjusting the pressure conditions in the synthesis unit 3.

The apparatus further comprises an interface 4 for controlling the process performed by the apparatus 1.

Example 1

In Example 1 the method according to the invention is performed using the apparatus 1. With regard to aminopropylation, the initial surface functionalization of fumed silica nanoparticles (fsNPs) as support material using 3-Aminopropyltriethoxysilane (APTES) is conducted based on [1] wherein drastic modifications regarding the applied technology and recipe are performed. The characterization of the APTES-functionalized fsNPs is investigated by means of the ninhydrin-assay and zeta potential measurements.

The method for the quantitative determination of primary amine with the ninhydrin reagent described, e.g., in [2] is slightly modified. Normal tap water is used instead of a MPC-buffer. The pH increase due to the applied APTES is adjusted to pH 7.5 with the saturated citric acid solution. The synthesis vessel 21, being a 300 L mixing tank ("SplitOmat"), is used for aminopropylation of fsNP wherein the applied conditions are 8.3 mL APTES per L reaction broth, ca. 50 g fsNP per L reaction broth, room temperature of 20.4° C. and 12 h incubation at maximum stirring speed of the stirrer 22.

With regard to sorption of laccase onto amino-fsNP, instead of using the produced amino-fsNP after exhaustive washing, the product is applied without any washing procedure. Laccase (1 U mg per amino-fsNP) is mixed with the reaction broth and incubated for 2 h at 5° C.

With regard to coupling of laccase and amino-fsNP, in 20 L-batches the sorbed laccase is immobilized onto the amino-fsNP using 10 mL glutaraldehyde per L reaction broth. This reaction is performed for 24 h under continuous mixing at room temperature (20.4° C.).

With regard to product cleaning or washing of the nanobiocatalysts, the product washing is performed using the filtration unit 3 as a single shaft disk filtration unit (SSDF, Novoflow) equipped with a plurality of ceramic filter discs (60 nm cut-off; 0.1 m2 filtration area) such as, e.g., three to seven filter discs, one peristaltic pump (feed), electric engine for spinning (30 Hz) and pressurized air system for back-flushing the filter discs 31.

The pressure of the filtration chamber is set at 0.5 bar and adjusted by a second peristaltic pump or the first pressure system. The filtrate runs to waste. During washing the retentate is in a closed loop with the incubation tank. For bottling the retentate is dispensed into a container by means of the second pump 52.

With regard to the aminopropylation Example 1 results in that the initial surface functionalization of fsNPs using APTES is conducted according to [1]. Therein, the authors showed that 0.8 µmol APTES per mg fsNP is enough modification agent to change the surface charge of the fsNPs to an extent which enhances the sorption and the enzyme immobilization. The aminopropylation of the fsNPs using APTES results in a positive zeta potential of 6.31±0.10 mV at pH 7 and a primary amine coverage of 8.35±0.29 mg $NH_2$ per g fsNP after 12 h of functionalization at room temperature.

Compared to the unfunctionalized fsNPs showing a negative zeta potential (−25.1±0.4 mV), a shift of 31.4 mV towards a positive charge is detected indicating a successful aminopropylation of the fsNPs. In comparison, the silanization performed by [1] resulted in a slightly lower zeta potential of 3.5±0.4 mV and an equal amount of amine moieties (8.03±0.41 mg $NH_2$ per g fsNP).

TABLE 1

Quality control of amynopropylated fsNPs in Example 1

| | Primary amine [a] [μmol [$NH_2$] $mg^{-1}$ [fsNP]] | [mg [$NH_2$] $g^{-1}$ [fsNP]] | Zeta potential[b] [mV] |
|---|---|---|---|
| fsNP | 0.00 ± 0.00 | 0.00 ± 0.00 | −25.1 ± 0.4 |
| APTES modified fsNP (Hommes et. al. 2011) | 0.50 ± 0.03 | 8.03 ± 0.41 | +3.5 ± 0.4* |
| 30 kg-APTES modified fsNP (1 h) | 0.21 ± 0.07 | 3.34 ± 1.07 | −10.0 ± 0.1 |
| 30 kg-APTES modified fsNP (12 h) | 0.52 ± 0.02 | 8.35 ± 0.29 | +6.3 ± 0.1 |

[a] Amount of primary amine moieties was determined performing the ninhydrin assay.
[b] Zeta potential was measured in SPB [pH 7].
*Surface charge at pH 7 of APTES modified fsNPs as reported by Hommes et al 2011.

Example 1 shows an improvement in chemical consumption. No buffered aqueous system is used during APTES modification. Therefore, phosphate (523 g disodium hydrogen phosphate per kg particle) and 50% of the citrate (ca. 15.1 g kg particle) could be saved.

Figure 2:
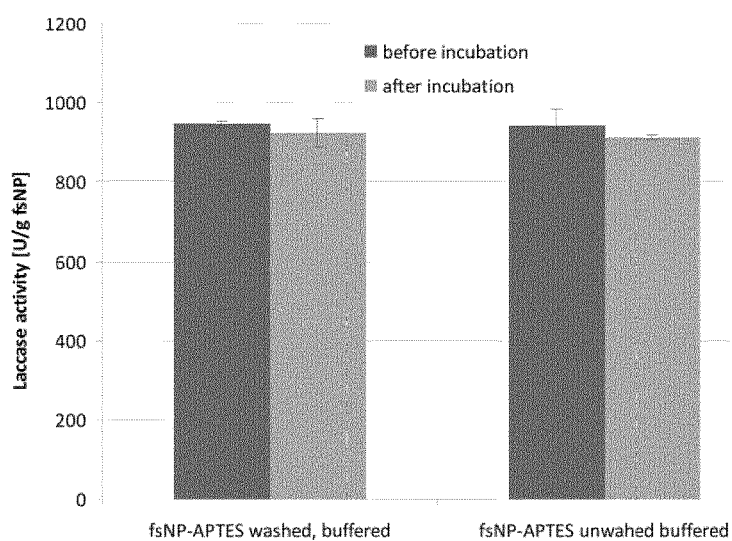
FIG. 2 shows a graph of a coupling test of aminopropylized fsNP of Example 1 buffered during enzyme coupling, comparison of washed and unwashed amino-fsNP.

FIG. 2 shows a test of washed and unwashed amino-fsNP providing that the final activity of the product is almost the same no matter whether the aminopropylized particle is washed or not.

The fact that no washing step is necessary increases the savings drastically. In total 31.78 kg disodium hydrogen phosphate and 1.6 kg citric acid can be saved. Additionally the water consumption is decreased by factor of 3 (−45 L per kg fsNP).

With regard to sorption of laccase onto amino-fsNP Example 1 results in that after the incubation (2 h; 2 times 20 L batches at room temperature and at 5°) no activity losses can be detected via ABTS assay (MPC-buffer; pH 3). The enzyme is stable in suspension ( ) at pH 7.5.

With regard to coupling of laccase and amino-fsNP Example 1 results in that after the enzyme is sorbed onto the amino-fsNP glutaraldehyde (200 mL) is mixed with the batch and continuously stirred during incubation (minimum 12 h, at 5° C. or room temperature). As showed in Table 2 12 h incubation is sufficient for the enzyme immobilization.

TABLE 2

Incubation time for enzyme immobilization of Example 1

| | Product activity after incubation [$U_{ABTS, pH3}$] | Final product activity after 3 washing cycles [$U_{ABTS, pH3}$] |
|---|---|---|
| Sample taken 2 hours after glutaraldehyde addition | 38465 | 33995 |
| Sample taken 12 hours after glutaraldehyde addition | 33695 | 42795 |

In order to quantitate the coupling efficiency the activity of the final product is measured for two different sample fractions: 1. Suspension and 2. supernatant; obtained after centrifugation at 21.000×g, 2 min.

The test results showed in Table 3 provide even a better distribution of activity between suspension and supernatant. Therefore, the coupling of laccase (genus *Thielavia*) can be performed at 20° C.

TABLE 3

Incubation temperature for enzyme immobilization in Example 1

| Incubation Temp. [° C.] | Activity in Suspension [U/L] | Activity in Supernatant [U/L] |
|---|---|---|
| 20.4 (RT) | 29221 | 38 |
| 5 | 26554 | 125 |

With regard to product cleaning and washing of the nanobiocatalyst Example 1 results in that the washing of the final product (20 L) is done continuously using the filtration unit 3 (SSDF) described above. The product is tested after washing it with 40 L tap water instead of using MPCbuffer. Thus, phosphate (523 g disodium hydrogen phosphate per kg particle) and citrate (30.35 g per kg particle) can be saved, again. The fact that no MPC-buffer is used for the continuous washing, these savings can be multiplied by the factor of 3 or even more. Additionally, the water consumption is decreased by the factor of 1.5 and 22.5 L water per kg fsNP can be saved.

The colour [$OD_{520\ nm}$] of the wastewater (filtrate) is used as an indicator for a sufficient washing process. The process is stopped until the $OD_{(520nm)}$ is below 0.1.

The activity of the final product is measured. Calculating the total recovery of activity after the whole process, almost 98% of the initially applied activity is recovered. Just 2% are lost due to liquid handling.

Concluding the above by using the method according to the invention with the improved protocol as in Example 1 it is possible to produce approximately 5 kg nanobiocatalyst per day. Furthermore, drastic improvements regarding resource savings could be achieved without loosing activity during the enzyme coupling process. Furthermore, the fact that the whole process can be performed at room temperature saves a lot of energy.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below. For example, it is possible to operate the invention in an embodiment wherein the synthesis unit and the filtration unit are implemented in one single unit.

The invention also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims ort the exemplary embodiments as well as subject matter comprising said features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range.

The present disclosure further comprises the following embodiments: Embodiment 1 is a method of producing nanobiocatalysts, comprising: suspending a support material in a liquid medium; functionalizing a surface of the support material by mixing the suspended support material with a functionalizer for a first predefined time at a first predefined temperature wherein a first broth results; applying a protein directly in the first broth after the first predefined time; mixing the protein with the first broth and incubating the protein for a second predefined time at a second predefined temperature wherein a second broth results; immobilizing the incubated protein onto the functionalized surface of the support material wherein a third broth results; filtering the third broth; and gathering a retentate of the filtering.

Embodiment 2 is the method of embodiment 1, wherein the support material is suspended in water.

Embodiment 3 is the method of embodiment 1 or 2, wherein the support material comprises fumed silica nanoparticles.

Embodiment 4 is the method of any one of embodiments 1 to 3, wherein the mixture of the suspended support material and the functionalizer comprises about $$1\frac{g}{L}$$

to about $$100\frac{g}{L}$$

fumed silica nanoparticles, preferably about $$40\frac{g}{L}$$

to about $$55\frac{g}{L}$$

fumed silica nanoparticles and particularly about $$50\frac{g}{L}$$

fumed silica nanoparticles.

Embodiment 5 is the method of any one of embodiments 1 to 4, wherein the functionalizer is an organosilane, preferably an Aminosilane and particularly 3-Aminopropyltriethoxysilane.

Embodiment 6 is the method of any one of embodiments 1 to 5, wherein the mixture of the suspended support material and the functionalizer comprises about 0.001 mM to about 1 mM functionalizer particularly about 0.18 mM to about 0.27 mM functionalizer.

Embodiment 7 is the method of any one of embodiments 1 to 6, wherein the first predefined time is in a range of about 1 minute to about 24 hours, preferably in a range of about 10 hours to about 15 hours and particularly is about 12 hours.

Embodiment 8 is the method of any one of embodiments 1 to 7, wherein the first predefined temperature is within a biologically compatible range, preferably in a range of about 4° C. to about 105° C., more preferably in a range of about 18° C. to about 25° C. and particularly in a range of about 20° C. to about 21° C.

Embodiment 9 is the method of any one of embodiments 1 to 8, wherein pH is adjusted to a predefined pH value when the suspended support material is mixed with the functionalizer for the first predefined time at the first predefined temperature.

Embodiment 10 is the method of embodiment 9, wherein the predefined pH value is within a biologically compatible range, preferably in a range of about 3 to about 9, more preferably in a range of about 7 to about 8 and particularly about 7.5.

Embodiment 11 is the method of embodiment 9 or 10, wherein pH is adjusted by applying a pH active compound and particularly a saturated citric acid solution.

Embodiment 12 is the method of any one of embodiments 1 to 11, wherein the protein is an enzyme.

Embodiment 13 is the method of embodiment 12, wherein the enzyme is laccase.

Embodiment 14 is the method of any one of embodiments 3 to 13, wherein the mixture of the first broth and the protein comprises about 0.01 mg to about 1 mg total protein per functionalized fumed silica nanoparticle and particularly about 0.15 mg total protein per functionalized fumed silica nanoparticle.

Embodiment 15 is the method of any one of embodiments 1 to 14, wherein the second predefined time is in a range of about 1 minute to about 24 hours, preferably in a range of about 1 hour to about 3 hours and particularly is about 2 hours.

Embodiment 16 is the method of any one of embodiments 1 to 15, wherein the second predefined temperature is within a biologically compatible range, preferably in a range of about 3° C. to about 7° C. and particularly about 5° C.

Embodiment 17 is the method of any one of embodiments 1 to 16, wherein the incubated enzyme is immobilized onto the functionalized surface of the support material by applying a immobilizer to the second broth and mixing the immobilizer and the second broth for a third predefined time at a third predefined temperature resulting in the third broth.

Embodiment 18 is the method of embodiment 17, wherein the immobilizer is a bifunctional crosslinker, particularly glutaraldehyde.

Embodiment 19 is the method of embodiment 18, wherein from about 0.001 mol to about 1 mol and particularly about 0.053 mol crosslinker is applied per liter of the second broth.

Embodiment 20 is the method of any one of embodiments 17 to 19, wherein the third predefined time is in a range of about 20 hours to about 30 hours and particularly is about 24 hours.

Embodiment 21 is the method of any one of embodiments 17 to 20, wherein the third predefined temperature is within a biologically compatible range, preferably in a range of about 18° C. to about 25° C. and particularly in a range of about 20° C. to about 21° C.

Embodiment 22 is the method of any one of embodiments 1 to 21, wherein the third broth is continuously filtered.

Embodiment 23 is the method of embodiment 22, wherein filtering of the third broth is performed by using a single shaft disk filtration unit.

Embodiment 24 is the method of embodiment 23, wherein the single shaft disk filtration unit comprises plural rotatable ceramic filter discs.

Embodiment 25 is the method of embodiment 24, wherein the single shaft disk filtration unit comprises a pressure air system arranged to remove retentate from the filter discs.

Embodiment 26 is the method of any one of embodiments 1 to 25, wherein a filtrate or permeate of the filtering of the third broth is disposed.

Embodiment 27 is the method of any one of embodiments 1 to 26, in which functionalizing of the surface of the support material, mixing the enzyme with the first broth and incubating the enzyme as well as immobilizing incubated enzyme onto the functionalized surface of the support material is performed in a synthesis container which is equipped with a stirrer.

Embodiment 28 is the method of embodiment 27 and any one of embodiments 22 to 26, wherein the single shaft disk filtration unit is connected to the synthesis container by a broth tube and by a retentate tube, wherein during filtering of the third broth the retentate is delivered from the single shaft disk filtration unit to the synthesis container via the retentate tube and the third broth is delivered from the synthesis tube to the single shaft disk filtration unit via the broth tube.

CITATION LIST

[1] G. Hommes, C. A. Gasser, C. B. C. Howald, R. Goers, D. Schlosser, P. Shahgaldian and P. F. X. Corvini (2012) "Production of a robust nanobiocatalyst for municipal wastewater treatment", Bioresource Technology, Available online 8 Dec. 2011, ISSN 0960-8524, 10.1016/j.biortech.2011.11.129

[2] S. W. Sun, Y. C. Lin, Y. M. Weng and M. J. Chen (2006) "Efficiency improvements on method for amino acid quantification". Journal of Food Composition and Analysis, 19, 112-117

The invention claimed is:

1. Method of producing nanobiocatalysts, the method comprising
suspending a support material comprising fumed silica nanoparticles in a liquid medium;
functionalizing a surface of the support material by mixing the suspended support material with a functionalizer being an Aminosilane for a first predefined time at a first predefined temperature, wherein a first broth results;
applying a protein being laccase directly in the first broth after the first predefined time;
mixing the protein with the first broth and incubating the protein for a second predefined time at a second predefined temperature, wherein a second broth results;
immobilizing the incubated protein onto the functionalized surface of the support material by applying an immobilizer being a bifunctional crosslinker with the second broth, wherein a third broth results;
filtering of the third broth; and
gathering a retentate of the filtering.

2. The method according to claim 1, wherein the support material is suspended in water.

3. The method according to claim 1, wherein the mixture of the suspended support material and the functionalizer comprises an amount of fumed silica nanoparticles in a range selected from: about $$1 \frac{g}{L}$$

to about $$100 \frac{g}{L};$$

and about $$40 \frac{g}{L}$$

to about $$55 \frac{g}{L}.$$

4. The method according to claim 1, wherein the method further comprises adjusting pH to a predefined pH value when the suspended support material is mixed with the functionalizer for the first predefined time at the first predefined temperature.

5. The method according to claim 4, wherein the predefined pH value is within a biologically compatible range selected from: about 3 to about 9; and about 7 to about 8.

6. The method according to claim 4, wherein the predefined pH value is about 7.5.

7. The method according to claim 4, wherein adjusting pH to a predefined pH comprises applying a pH active compound.

8. The method according to claim 7, wherein the pH active compound is a saturated citric acid solution.

9. The method according to claim 1, wherein the mixture of the first broth and the laccase comprises about 0.01 mg to about 1 mg total laccase per functionalized fumed silica nanoparticle.

10. The method according to claim 1, wherein the second predefined temperature is within a biologically compatible range of about 3° C. to about 7° C.

11. The method according to claim 1, wherein immobilizing the incubated laccase onto the functionalized surface of the support material comprises:
applying the immobilizer to the second broth; and
mixing the immobilizer and the second broth for a third predefined time at a third predefined temperature resulting in the third broth.

12. The method according to claim 11, wherein the third predefined time is in a range of about 20 hours to about 30 hours.

13. The method according to claim 11, wherein the bifunctional crosslinker is glutaraldehyde and the glutaraldehyde is applied to the second broth in an amount of about 0.001 mol to about 1 mol per liter of the second broth.

14. The method according to claim 11, wherein the bifunctional crosslinker is glutaraldehyde and the glutaraldehyde is applied to the second broth in an amount of about 0.053 mol per liter of the second broth.

15. The method according to claim 11, wherein the third predefined time is about 24 hours.

16. The method according to claim 11, wherein the third predefined temperature is within a biologically compatible range selected from: about 18° C. to about 25° C.; and about 20° C. to about 21° C.

17. The method according to claim 1, wherein the third broth is continuously filtered.

18. The method according to claim 17, wherein a single shaft disk filtration unit is connected to a synthesis container by a broth tube and by a retentate tube, wherein during filtering of the third broth the retentate is delivered from the single shaft disk filtration unit to the synthesis container via the retentate tube and the third broth is delivered from the synthesis tube to the single shaft disk filtration unit via the broth tube.

19. The method according to claim 1, wherein functionalizing the surface of the support material, mixing the laccase with the first broth and incubating the laccase, as well as immobilizing the laccase enzyme onto the functionalized surface of the support material, are performed in a synthesis container which is equipped with a stirrer.

20. The method according claim 19, wherein filtering the third broth is performed using a single shaft disk filtration unit.

21. The method according to claim 20, wherein the single shaft disk filtration unit comprises plural rotatable ceramic filter discs.

22. The method according to claim 21, wherein the single shaft disk filtration unit comprises a pressure air system arranged to remove retentate from the filter discs.

23. The method according to claim 1, wherein the mixture of the suspended support material and the functionalizer comprises fumed silica nanoparticles in an amount of about $$50\frac{g}{L}.$$

24. The method according to claim 1, wherein the Aminosilane is 3-Aminopropyltriethoxysilane.

25. The method according to claim 1, wherein the mixture of the first broth and the laccase comprises about 0.15 mg total laccase per functionalized fumed silica nanoparticle.

26. The method according to claim 1, wherein the second predefined temperature is about 5° C.

* * * * *